United States Patent
Van Der Kamp et al.

(10) Patent No.: US 9,248,223 B2
(45) Date of Patent: *Feb. 2, 2016

(54) INSERT FOR A BREAST PUMP

(75) Inventors: Gertrude Riette Van Der Kamp, Groningen (NL); Johannes Tseard Van Der Kooi, Hurdegaryp (NL); Klaas Kooijker, Drachten (NL)

(73) Assignee: Koninklijke Philips N.V., Eindhoven (NL)

( * ) Notice: Subject to any disclaimer, the term of this patent is extended or adjusted under 35 U.S.C. 154(b) by 268 days.

This patent is subject to a terminal disclaimer.

(21) Appl. No.: 13/256,539

(22) PCT Filed: Mar. 22, 2010

(86) PCT No.: PCT/IB2010/051222
§ 371 (c)(1),
(2), (4) Date: Sep. 14, 2011

(87) PCT Pub. No.: WO2010/109398
PCT Pub. Date: Sep. 30, 2010

(65) Prior Publication Data
US 2012/0004604 A1 Jan. 5, 2012

(30) Foreign Application Priority Data
Mar. 26, 2009 (EP) .................................... 09156300

(51) Int. Cl.
*A61M 1/06* (2006.01)
(52) U.S. Cl.
CPC *A61M 1/06* (2013.01); *A61M 1/066* (2014.02)
(58) Field of Classification Search
CPC ...... A61M 1/06; A61M 1/066; A61M 1/0072
USPC ....................................... 604/72–74, 317, 346
See application file for complete search history.

(56) References Cited

U.S. PATENT DOCUMENTS

| 4,249,481 A | 2/1981 | Adams |
| 4,680,028 A | 7/1987 | Stuart |
| 4,772,262 A | 9/1988 | Grant et al. |
| 5,049,126 A | 9/1991 | Larsson |
| 6,383,163 B1 | 5/2002 | Kelly et al. |
| 6,461,324 B1 | 10/2002 | Schlensog |
| 6,579,258 B1 | 6/2003 | Atkin |

(Continued)

FOREIGN PATENT DOCUMENTS

| FR | 1067421 | 6/1954 |
| FR | 1067421 A | 6/1954 |

(Continued)

*Primary Examiner* — Nicholas Lucchesi
*Assistant Examiner* — Melissa A Snyder

(57) ABSTRACT

The present invention relates to an insert adapted to fit on a breast-receiving funnel of a breast pump. The insert comprises a circumferentially extending resiliently deformable wall which defines a teat receiving space and against which a user's teat is locatable, the insert being configured to define a pressure chamber between the resiliently deformable wall and a breast receiving funnel when the insert is fitted on a breast receiving funnel, wherein said wall is configured to deform towards a user's teat located in the teat receiving space in a predetermined manner when a pressure difference is applied between the teat receiving space and the pressure chamber such that a peristaltic action is applied to a user's teat, to aid the expression of milk therefrom.

15 Claims, 7 Drawing Sheets

(56) References Cited

U.S. PATENT DOCUMENTS

| | | |
|---|---|---|
| 6,887,218 B2 | 5/2005 | Warburton |
| 7,101,350 B2 | 9/2006 | Ytteborg |
| 7,972,297 B2 * | 7/2011 | Bryan et al. .................. 604/74 |
| 8,052,635 B1 * | 11/2011 | Kelly et al. .................. 604/74 |
| 2002/0198489 A1 | 12/2002 | Silver et al. |
| 2004/0087898 A1 | 5/2004 | Weniger |
| 2005/0043677 A1 | 2/2005 | Kelly et al. |
| 2005/0234370 A1 | 10/2005 | Beal et al. |
| 2007/0088250 A1 | 4/2007 | Silver et al. |

FOREIGN PATENT DOCUMENTS

| | | |
|---|---|---|
| GB | 660283 | 11/1951 |
| GB | 2340755 A | 3/2000 |
| GB | 2340755 B | 9/2002 |
| JP | 53120881 A | 10/1978 |
| JP | 2005502397 A | 1/2005 |
| WO | 03000313 A1 | 1/2003 |

* cited by examiner

INSERT FOR A BREAST PUMP

FIELD OF THE INVENTION

The present invention relates to an insert for a breast pump. In particular, the present invention relates to an insert adapted to fit on a breast receiving funnel of a breast pump operable to extract milk from a user. The present invention also relates to a breast receiving funnel for a breast pump and a breast pump comprising a breast-receiving funnel.

BACKGROUND OF THE INVENTION

Breast pumps are well known devices for extracting milk from a breast of a user. A breast pump may be used if the baby is not itself able to extract the milk, or if the mother is separated from the baby, for example if away from the baby at work. The use of a breast pump to extract milk may also be used to stimulate lactation in women with a low milk supply.

Conventional breast pumps make use of a vacuum to induce milk extraction from a nursing mother's breast. The pumping action of the device draws the milk from the teat to a collection vessel, and may be adjusted to the preferences of the lactating female.

A conventional breast pump for extracting milk from a user's breast is shown in FIG. 1. Such a conventional breast pump unit 1 comprises a main body 2 and a feeding bottle 3. The feeding bottle 3 is attached to the main body 2 by a screw fitting.

A vacuum pump unit (not shown) is formed in the main body 2 to create a vacuum, as will be described hereinafter and a handle 4 extends from the main body 2. Breast pumps may be manually operated, for example by squeezing the handle or by operation of a foot pedal. Breast pumps may also be electrically driven by a small electric motor.

A breast receiving funnel 5 is fixedly attached to the main body 2 for receiving the breast of a user. The funnel 5 comprises a mouth 6 and a throat 7. The mouth 6 is open at an upper end and an inner surface of the mouth 6 converges from the upper end towards the throat 7 to form a hollow recess. An insert 8 is insertable in the mouth 6 of the funnel 5 in an attempt to improve a user's comfort and aid the expression of milk.

However, a problem with conventional breast pumps is that users are known to suffer from discomfort or difficulty when using such a conventional breast pump. When an infant feeds from its mother's breast, the baby applies two actions to obtain milk, a sucking action and a peristaltic movement created by the action of the infant's tongue on the teat of the mother's breast, the teat comprising a nipple and areola tissue. The sucking action applies a negative pressure to latch onto the breast and induce milk flow. The infant can also perform a peristaltic stripping motion over the areola and nipple to induce milk flow from the breast. In this motion a rhythmic contraction and expansion motion is performed to induce the milk flow.

The peristaltic (tongue) motion stimulates the hormone-production responsible for the 'let-down' reflex which allows milk produced in the milk glands to be released into the milk ducts. Conventional breast pumps do not produce this peristaltic motion, and so a high negative pressure is required to obtain a flow of milk to compensate for the lack of peristaltic movement. Furthermore, the absence of such an action means that extracting milk is uncomfortable and inefficient and does not provide a natural action.

Breast pumps with inserts are disclosed in U.S. Pat. No. 4,249,481 which attempt to apply a peristaltic motion to a breast. However, each of the breast pumps with inserts disclosed in this document have a complicated construction, for example necessitating the use of a double wall insert and applying a pressure differential between the walls of the insert. Therefore, the arrangements shown in this document require a complex construction, such as a plurality of pressure ports, and make it difficult to clean the insert and associated breast pump.

SUMMARY OF THE INVENTION

Therefore, it is an object of the invention to provide a breast pump which substantially alleviates or overcomes the problems mentioned above and aids the expression of breast milk from a breast in a way that is more analogous to the action of a suckling infant.

Accordingly, the present invention provides an insert adapted to fit on a breast-receiving funnel of a breast pump comprising a circumferentially extending resiliently deformable wall which defines a teat receiving space and against which a user's teat is locatable, the insert being configured to define a pressure chamber between the resiliently deformable wall and a breast receiving funnel when the insert is fitted on a breast receiving funnel, wherein said wall is configured to deform towards a user's teat located in the teat receiving space in a predetermined manner when a pressure difference is applied between the teat receiving space and the pressure chamber such that a peristaltic action is applied to a user's teat, to aid the expression of milk therefrom.

Advantageously, the wall is configured to deform towards a user's teat located in the teat receiving space in a predetermined manner when a negative pressure is applied in the teat receiving space such that a peristaltic action is applied to a user's teat.

Preferably, the teat receiving space has an opening for receiving a user's teat, and the stiffness of the wall proximate to the opening is lower than the stiffness of the resiliently deformable wall distal to the opening.

In one embodiment, the resiliently deformable wall has a diverging wall thickness which increases away from said opening such that a thinner portion of said wall deforms towards said user's teat located in said teat receiving space prior to a thicker portion of said wall deforming towards said user's teat.

Preferably, a first portion of said wall disposed proximate to the opening is configured to deform towards a user's teat located in said teat receiving space prior to a second portion of said wall distal to said opening deforming towards a user's teat.

In one embodiment, the first portion of said wall is an elliptical frustum shape and the second portion is a cylindrical shape such that, when a pressure difference is applied between the teat receiving space and the pressure chamber, the first portion deforms towards said user's breast to apply a positive pressure thereto prior to the second portion deforming towards said user's breast.

In one embodiment, the first portion of said wall is formed from a material with a lower stiffness coefficient to the material forming the second portion of said wall.

The resiliently deformable wall may extend between mounting means for mounting the insert to a breast receiving funnel which extend circumferentially around upper and lower ends of the wall.

Conveniently, at least one rib extends longitudinally along the resiliently deformable wall to control the collapse of said wall towards the teat.

According to another aspect of the invention, there is provided a breast receiving funnel for a breast pump with an insert integrally formed therewith.

The breast receiving funnel may comprise a rigid outer shell and a pressure chamber formed between the resiliently deformable wall and the rigid outer shell, the pressure chamber extending around the resiliently deformable wall.

Advantageously, a fluid inlet is formed through the rigid outer shell such that the pressure chamber is open to atmospheric air external to the breast receiving funnel.

Conveniently, the insert is removably mounted to the funnel.

According to another aspect of the invention, there is provided a breast pump comprising a breast receiving funnel with an insert integrally formed therewith, the breast pump including means for generating a negative pressure in the funnel when a user's breast is received therein.

Preferably, the breast pump further comprises means to apply a positive pressure in said pressure chamber to urge the resiliently deformable wall to deform towards a user's teat when the pressure in said pressure chamber is increased.

BRIEF DESCRIPTION OF THE DRAWINGS

Preferred embodiments of the invention will now be described, by way of example only, with reference to the accompanying drawings, in which.

DETAILED DESCRIPTION OF THE EMBODIMENTS

Figure 1:
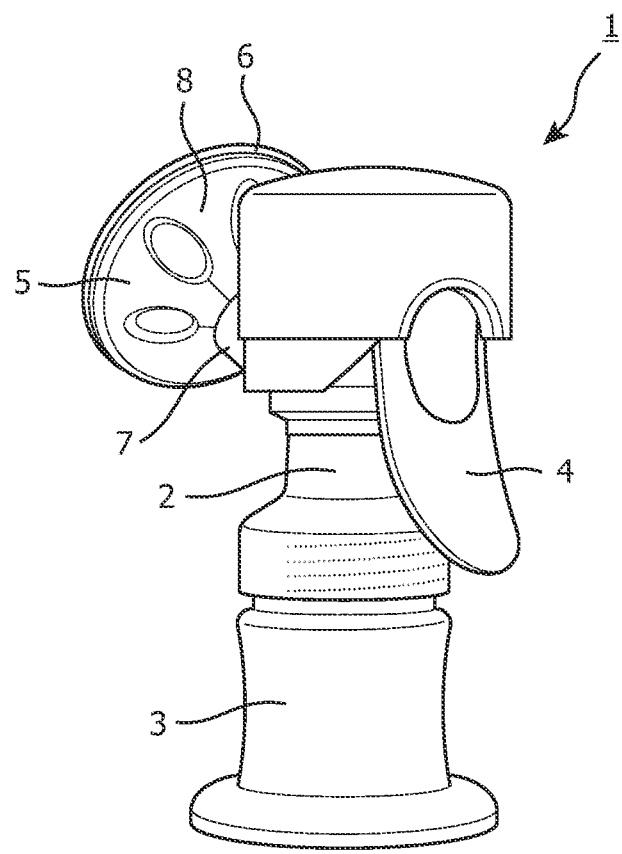
FIG. 1 illustrates a perspective view of an existing breast pump.
Figure 2:
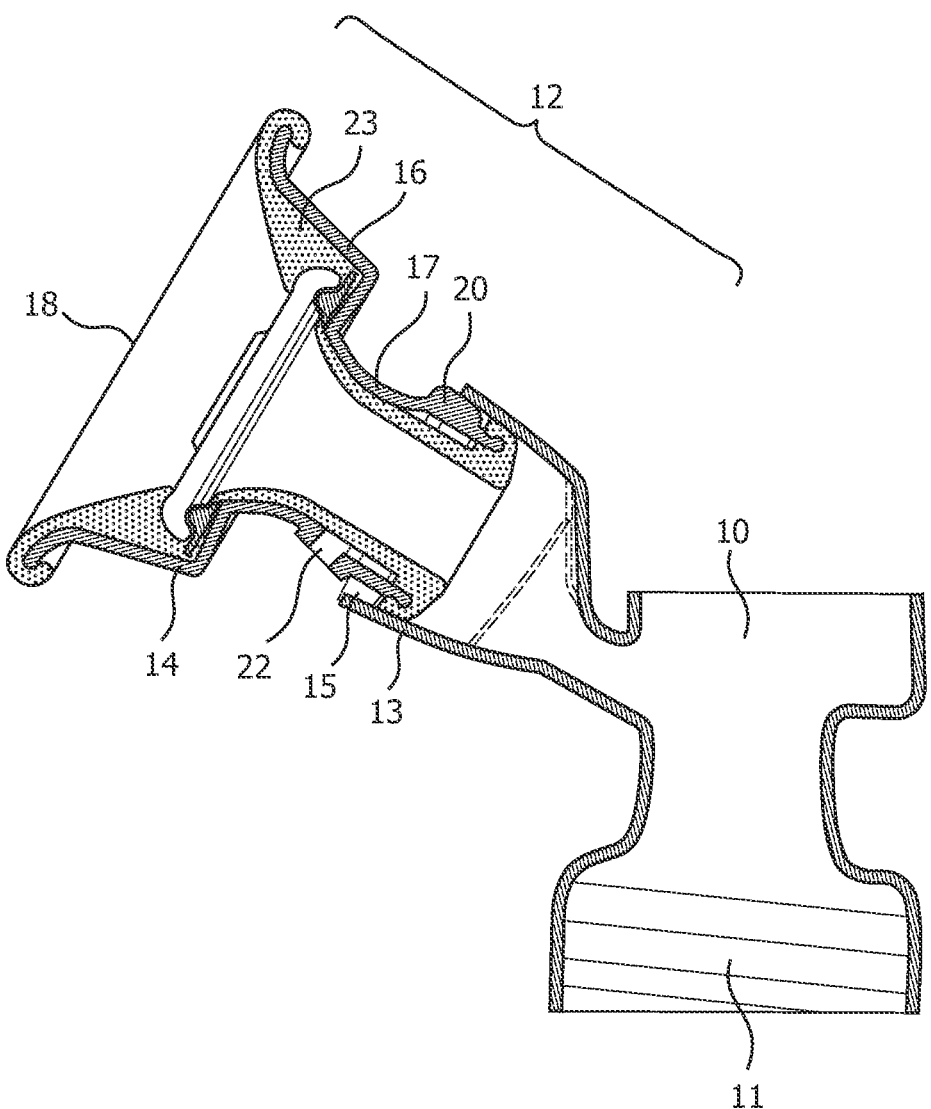
FIG. 2 illustrates a cross-sectional side view of a breast receiving funnel and an insert for a breast pump according to a first embodiment of the present invention.
Figure 3:
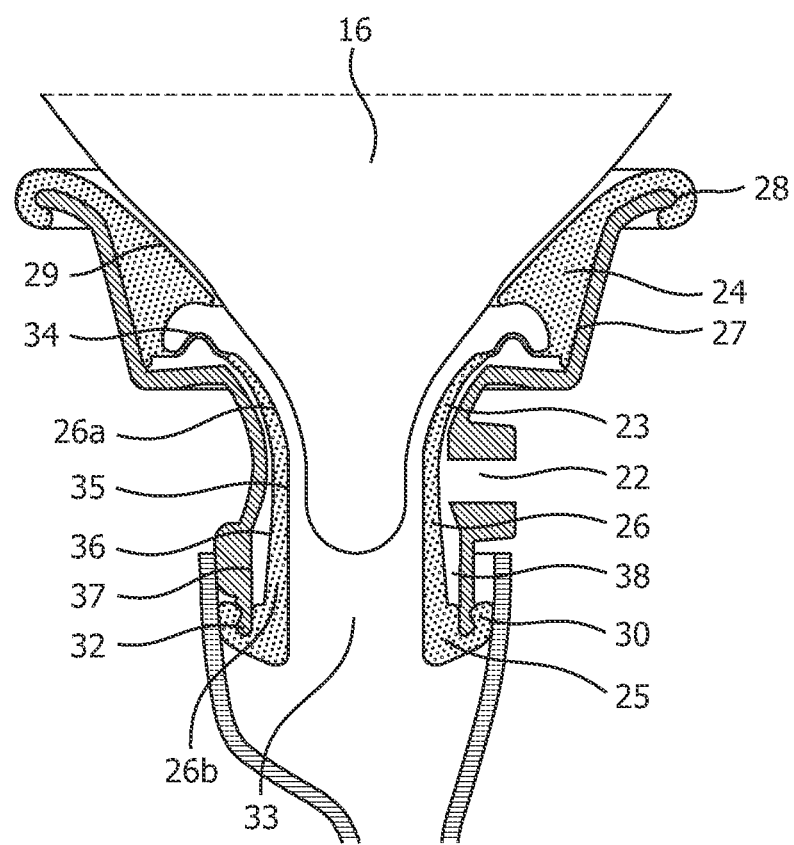
FIG. 3 illustrates a cross-sectional side view of the breast receiving funnel and insert shown in FIG. 2.

Referring now to the drawings, in particular FIGS. 2 and 3, a breast pump unit is shown comprising a main body 10 and a milk-receiving vessel (not shown). The milk receiving vessel, which may take the form of a feeding bottle for an infant or baby, is attached to the main body 10 by a screw fitting 11, although it will be understood that alternative releasable attachment means may be used, such as clips (not shown).

A vacuum pump unit (not shown) is disposed in the main body 10, to create a vacuum, as will be described hereinafter and a handle (not shown) extends from the main body 10. The vacuum pump unit (not shown) is motorized and the handle operates a motorized vacuum pump unit (not shown) which is powered by batteries disposed in the main body 10. Alternatively, the handle is manually operable to operate the vacuum pump unit. The vacuum pump unit (not shown) is conventional and so no further description of the pump unit will be given here.

A breast receiving funnel 12 extends from the main body 10 of the breast pump for receiving the breast of a user. The funnel 12 comprises a first shell section 13 and a second shell section 14. The first shell section 13 extends from the main body 10 and is integrally formed therewith. The first shell section 13 defines a tube which communicates with the vacuum pump unit at one end and has an opening 15 at the end distal to the main body 10.

The second shell section 14 comprises a mouth 16 and a throat 17. The mouth 16 is open at an upper end 18 and an inner surface of the mouth 16 converges from the upper end 18 towards the throat 17 to form a hollow recess. A lower end of the throat 17, distal to the mouth 16, is removably mountable in the first shell section opening 15 and a mounting ridge 20 is formed around the lower end of the throat 17 to locate and fixedly hold the lower end of the second shell section 14 in the first shell section 13. A fluid inlet 22 is formed through the throat 17 of the second shell section 14, for reasons that will become apparent hereinafter. The first and second shell sections 13,14 are formed from a rigid, non-deformable material, such as a rigid plastic.

Although in the present embodiment the first shell section 13 of the funnel 12 is fixedly mounted to the main body 10 of the breast pump 1, it will be understood that in an alternative embodiment both the first and second sections of the funnel 12 are removable therefrom. Such a funnel 12 is removably mounted to the main body 10 of the breast pump 1 to aid cleaning or sterilization of the funnel 5 and main body 2. Furthermore, although in the present invention the funnel 12 comprises separate first and second shell sections 13,14 to aid assembly and cleaning, it will be appreciated that in an alternative embodiment the funnel is a one piece construction comprising an outer shell defined by the integrally formed first and second shell sections.

The first and second shell sections 13,14 of the funnel 12 form a funnel outer shell which defines a hollow passage communicating the main body 10 with the mouth 16 such that a fluid passageway is provided between the hollow recess of the funnel 12 and the milk receiving vessel (not shown). The hollow passage also provides a passageway to enable the vacuum pump unit (not shown) disposed in the main body 10 to create a negative pressure in the funnel 12 when a user's breast is disposed therein, as will be explained below.

Referring to FIGS. 2 and 3, an insert 23 adapted to fit on the breast-receiving funnel 12 of the breast pump 1 is shown. The insert 23 is removably insertable in the second shell section 14 of the breast receiving funnel 12. An advantage of this arrangement is that it enables the insert 23 to be removed from the funnel 12 and so the funnel 12 and insert 23 can be easily cleaned and/or sterilized. The insert 23 is formed from a resilient material, such as a suitable rubber, silicone elastomer or latex material. Alternatively, the insert is formed from a thermoplastic elastomer.

The insert 23 comprises an upper part 24, a lower part 25 and a circumferentially extending, resiliently deformable wall 26 extending therebetween. The upper part 24 of the insert 23 is located in the mouth 16 of the second shell section 14 when the insert 23 is disposed in the funnel 12 and an outer face 27 of the upper part 24 locates against an inner surface of the mouth 16 of the second shell section 14. The upper part 24 extends over a rim of the upper end 18 of the second shell section 14 and an outer edge of the upper part 24 is turned back on itself to form a lip 28 to co-operate with said rim and fixedly mount the upper part 24 to the second shell section 14. Therefore, the upper part 24 is sealed against the second shell section 14. An inner surface 29 of the insert upper part 24 converges on itself to form a conically-shaped hollow section for receiving a user's breast as will become apparent hereinafter.

The lower part 25 of the insert 23 is located at the lower end of the throat 17 when the insert 23 is disposed in the funnel 12 and has a circumferentially extending lip 30 formed by an edge of the lower part 25 being turned back on itself. This lip 30 extends over a rim of the lower end of the second shell section 14 and co-operates with said rim to fixedly mount the lower part 25 to the second shell section 14. Therefore, the lower part 25 is sealed against the second shell section 14.

Figure 6:
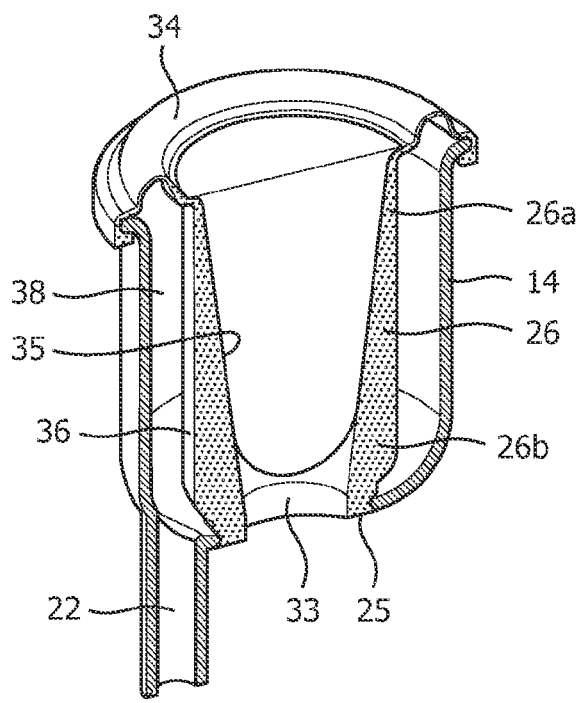
FIG. 6 illustrates a schematic cut-away perspective view of the insert shown in FIG. 2.
Figure 7:
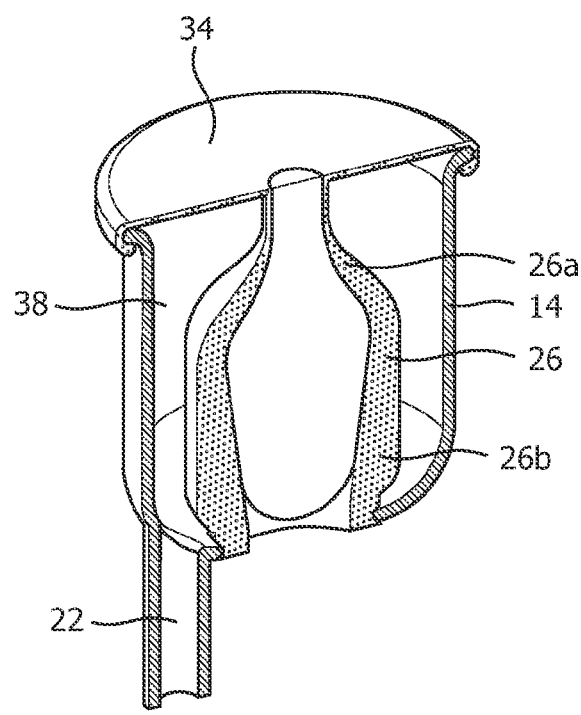
FIG. 7 illustrates another schematic cut-away perspective view of the insert shown in FIG. 6 with the resiliently deformable wall shown partially deformed.
Figure 8:
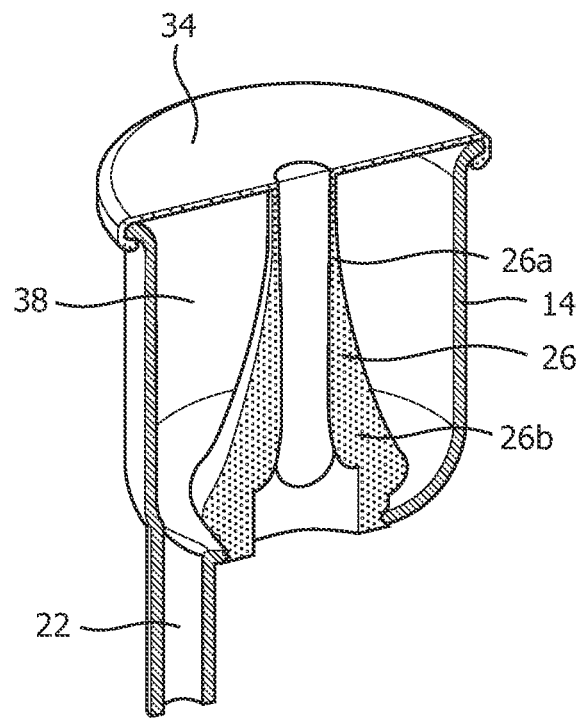
FIG. 8 illustrates another schematic cut-away perspective view of the insert illustrated in FIG. 6 with the resiliently deformable wall shown fully deformed.

Although in the above embodiment, the insert 23 is removably mountable in the second shell section 14 by the insert upper and lower parts 24,25 respectively overlapping and mounting to the upper and lower end rims of the second shell section 14 due to the resiliently deformable nature of the insert 23, it will be understood that the invention is not limited thereto and that in alternative embodiments the insert 23 extends into the second shell section and is fixedly mounted by an adhesive. Furthermore, if the first and second shell sections 13,14 are integrally formed, the insert lower part 25 can be configured to mount to a shoulder extending from the outer shell, as shown in FIGS. 6 to 8.

The circumferentially extending, resiliently deformable wall 26 extends between the insert upper and lower parts 25,26 and defines a teat receiving space 33 therein. A user's teat comprising a nipple and areola tissue is inserted into the teat receiving space 33 defined by the resiliently deformable wall 26 during use of the insert 23, as will be explained in detail hereinafter.

A flexible corrugated membrane 34 is formed at the upper end of the resiliently deformable wall 26 which extends circumferentially and is integrally formed with the upper part 24 of the insert 23. The upper end of the resiliently deformable wall 26 distends outwardly to said corrugated membrane 34, such that said upper end of the resiliently deformable wall 26 can deform inwardly, as will be explained hereinafter.

The resiliently deformable wall 26 has a wall thickness which varies along its length from the insert upper part 24 to the insert lower part 25. The teat receiving space 33 extends to the first shell section 13, which enables milk expressed from a user's breast to be expelled from the insert 23.

An inner surface 35 of the resiliently deformable wall 26 and an outer surface 36 of the resiliently deformable wall 26 diverge away from each other from the insert upper part 24 to the insert lower part 25, and so the wall thickness of the resiliently deformable wall increases from an upper end of the teat receiving space 33 thereof.

As the thickness of the resiliently deformable wall 26 increases along its length the stiffness of the wall 26 increases, such that the wall is less deformable towards the lower end of said teat receiving space 33.

When the insert is disposed in the funnel 12, the outer surface 36 of the resiliently deformable wall 26 and an inner surface 37 of the second shell section 14 define a pressure chamber 38 therebetween, which will be described in detail below.

The upper and lower parts 24, 25 of the insert 23 seal against the second shell section 14 to define the respective upper and lower extents of the pressure chamber 38, as will become apparent below.

Figure 4:
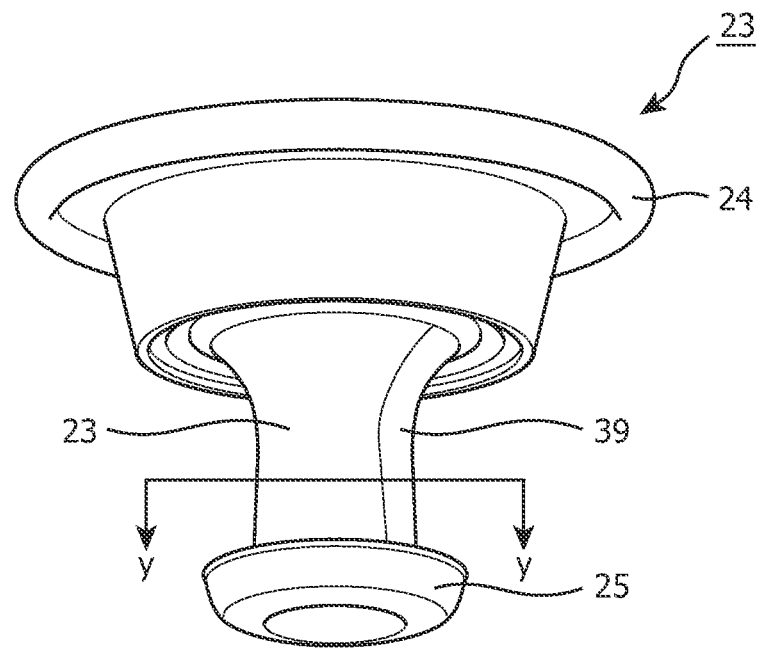
FIG. 4 illustrates a schematic perspective view of the insert shown in FIG. 3.
Figure 5:
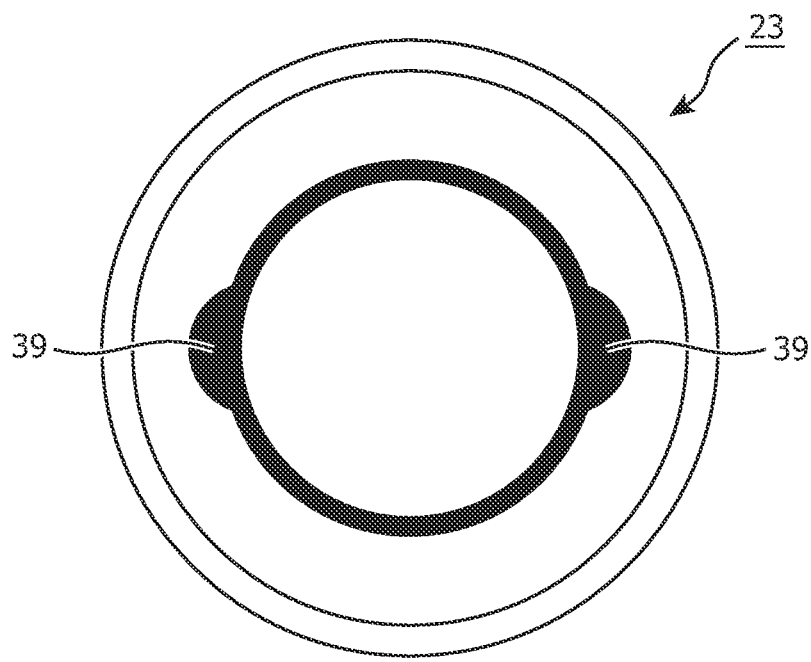
FIG. 5 illustrates a schematic cross-sectional view of the insert shown in FIG. 4 along the line Y-Y.

Referring to FIGS. 4 and 5, a pair of diametrically opposing ribs 39 extend longitudinally along the outer surface 36 of the resiliently deformable wall 26. The ribs 39 are integrally formed with the wall 26 and provide local thickening so as to increase the stiffness of the wall therealong. Therefore, when the wall is urged to deform and collapse inwardly into the teat receiving space 33, as will be explained hereinafter, the ribs 39 provide local stiffness along the length of the wall 26 and so wall deforms into an ellipse-like shape due to the portion of the wall distal to the ribs having a lower stiffness.

An advantage of this rib arrangement is that the pressure applied by the insert 23 on the teat disposed in the teat receiving space 33 is non-circular, due to the elliptical collapse of the wall 26 which is analogous to the pressure and action applied by an infant, and so a user is able to change the pressure points on the teat by rotating the breast pump to aid the expression of milk therefrom and to increase comfort. Furthermore, the ribs control the collapse of the insert towards the teat. This prevents the insert from forming spaces and wrinkles which can pinch the nipple and so cause pain to a user.

Operation of the breast pump 1 and the insert 23 according to the above exemplary embodiment will now be described with reference to FIGS. 3 to 8.

A user inserts the insert 23 into the second shell section 14 of the funnel 12; the insert 23 deforming due to its resilient nature to allow insertion. The insert upper part 24 locates against the inner surface of the mouth 16 and the extends over the rim of the second shell section 14 and the lip 28 co-operates with said rim to fixedly mount the upper part 24 to the second shell section 14.

Similarly, the insert lower part 25 locates against the lower end of the throat 17 and the circumferentially extending lip 30 extends over the rim of the lower end of the second shell section 14 and co-operates therewith to fixedly mount the lower part 25 to the second shell section 14. The outer surface 36 of the resiliently deformable wall 26 and an inner surface 37 of the second shell section 14 are spaced from each other to form the pressure chamber 38 which extends circumferentially around the resiliently deformable wall 26 and so circumferentially encompasses the teat receiving space 33.

The fluid inlet 22 provides a fluid communication between the pressure chamber 38 and atmospheric air external to the breast pump. However, in an alternative embodiment the fluid inlet 22 is connected to pressure means (not shown), such as an air pump, to provide a positive pressure differential in the pressure chamber, as will be explained below. Although a breast pump is described above which is specially configured to receive an insert as described in detail above, it will be understood that in an alternative embodiment the insert is configured for use with a conventional breast pump. For example, in an alternative embodiment a passageway is formed in the insert to allow a fluid communication between atmospheric air outside the inlet to the pressure chamber.

Once the insert 23 is inserted in the second shell section 14 of the breast receiving funnel 12, a user then inserts the lower end of the throat 17 of said second shell section 14 into the opening 15 of the first shell section 13. The mounting ridge 20 formed around the lower end of the throat 17 locates and fixedly holds the second shell section 14 in the first shell section 13 and the circumferentially extending lip 30 of the insert lower part 25 is disposed against an inner surface of the first shell section 13 to seal the first and second shell sections 13,14.

The breast pump 1 and insert 23 are then in an assembled state and the user inserts a breast into the mouth 16 of the funnel second shell section 14. The user's areola and/or breast is disposed in the conically-shaped hollow section formed by the upper part 24 and locates and seals against the inner surface 29 of said insert upper part 24. Hence, the user's teat is inserted into the insert 23 and is disposed in the teat receiving space 33 such that the teat locates proximate the inner surface 35 of the wall 26.

A negative pressure is formed in the teat receiving space 33 by operating the vacuum pump unit (not shown). The negative pressure helps to induce milk extraction from the user's breast in the manner of a conventional breast pump by applying a negative pressure to the teat, and helps to maintain the breast pump 1 in position relative to the breast even when little or no support is provided externally.

When a negative pressure is applied in the teat receiving space 33, the teat is extruded into the teat receiving space 33 such that a substantial portion of the surface of the teat disposed in the teat receiving space 33 is proximate to the inner surface 35 of the resiliently deformable wall 26 of the insert 23.

As the negative pressure is applied in the teat receiving space 33, a pressure differential is formed between the teat receiving space 33 and the pressure chamber 38, which is at atmospheric pressure due to the fluid inlet 22 providing a fluid communication with atmospheric air.

The pressure differential between the teat receiving space 33 and the pressure chamber 38 causes the resiliently deformable wall 26 to distend inwardly into the teat receiving space 33. Due to the varying wall thickness of the resiliently deformable wall 26, wherein the wall thickness increases from an thinner portion 26a of the wall proximate the upper part 24 of the insert to a thicker portion 26b of the wall proximate to the lower part 25 of the insert, the wall proximate to the upper part 24 has a low stiffness which increases towards the lower part 25.

Therefore, as the pressure differential between the teat receiving space 33 and the pressure chamber 38 increases, the thinner portion 26a of the resiliently deformable wall 36 is caused to distend inwardly into the teat receiving space 33, and the higher stiffness of the thicker portion 26b prevents said thicker portion from deforming initially (refer to FIG. 7). Subsequently, as the pressure difference increases, a greater portion of the wall 26 is progressively caused to deform and distend inwardly into the teat receiving space 33. Therefore, the wall 26 is caused to progressively distend inwardly from one end of the teat receiving space towards the other end thereof.

As the thinner portion 38a of the resiliently deformable wall 26 is caused to distend inwardly, the flexible corrugated membrane 34 is caused to expand. This is possible due to the resilience of the membrane and the corrugation of the membrane being drawn out (refer to FIGS. 6 to 8).

The progressive deformation of the resiliently deformable wall 26 due to the varying thickness of the wall 26 as the pressure in the teat receiving space is lowered causes the insert 23 to impart a peristaltic action on a user's nipple and areola which promotes the expression of milk from a user's nipple and is more analogous to an infant or baby compared with a conventional breast pump action. Furthermore, an advantage of the present invention is that it is only necessary to create a vacuum in the teat receiving space in order for the resiliently deformable wall 26 to distend. Milk is therefore expressed from the user's breast and is expelled from the funnel 12 through the passageway defined by the first and second shell sections 13,14 of the funnel 12 into the main body of the breast pump 1 and into the milk receiving vessel 3.

To cause the resiliently deformable wall 26 to distend outwardly into its original position the pressure in the teat receiving space 33 is increased to reduce the pressure differential. Therefore, the resiliently deformable wall 26 is urged to distend outwardly into its original position, away from the teat, due to the resilient nature of the wall 26. As the pressure differential is reduced, the thicker portion 26b of the wall 26 returns to its original shape and position, prior to the thinner portion 26a returning to its original shape and position.

By cyclically generating a pressure difference between the pressure chamber 38 and the teat receiving space 33, a repeated peristaltic action is imparted on a user's teat disposed in the insert 23. Therefore, the negative pressure applied in the teat receiving space is less than that required to obtain milk using a conventional breast pump due to the application of the peristaltic movement. Furthermore, when the wall 26 deforms inwardly, the section of the nipple and areola exposed to the negative air pressure in the teat receiving space 33 is reduced and so the vacuum level perception is reduced.

The insert 23 is removable from the second shell section 14 when said second shell section is removed from the first shell section 13 due to the deformable nature of the insert 23, wherein the upper and lower parts 24,25 of the insert 23 can be manipulated to disengage them from the second shell section rims, although other arrangements for removably mounting the insert 23 to the outer shell of the funnel 12 are envisaged. An advantage of the insert 23 being removable from the funnel 12 is that the insert is easy to clean. Furthermore, due to the limited number of components of the insert, the insert and breast pump assembly is easy to assemble and simple to manufacture.

A second exemplary embodiment of the invention will now be described with reference to FIGS. 9 and 10. In this embodiment, the insert and the breast pump configured to receive the insert are generally the same as for the first embodiment, and so a detailed description is omitted herein. Elements of the insert and breast pump which are generally the same as for the first exemplary embodiment retain the same reference numerals, and the insert is used with a breast pump as shown in FIG. 3. However, in this embodiment the shape of the resiliently deformable wall in cross-section is varied.

Figure 9:
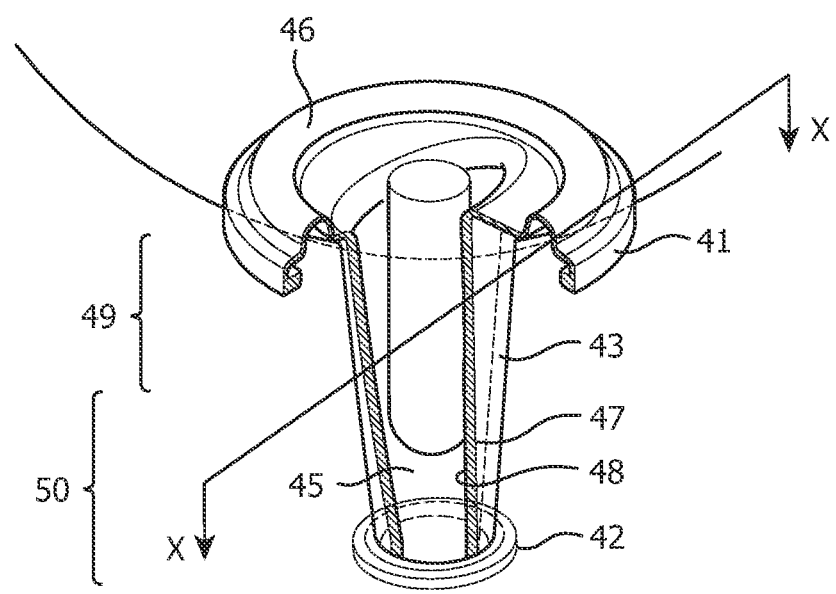
FIG. 9 illustrates a schematic cut-away perspective view of an insert for a breast pump with a resiliently deformable wall according to a second embodiment of the present invention.
Figure 10:
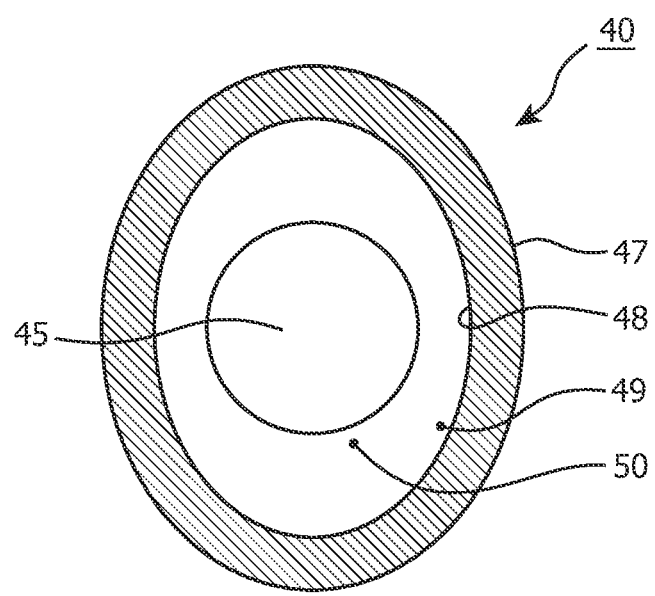
FIG. 10 illustrates a schematic cross-sectional view of the insert shown in FIG. 9 along the line X-X.

Referring now to FIGS. 9 and 10, an insert 40 adapted to fit on the breast-receiving funnel 12 of the breast pump 1 is shown. The insert 40 is removably insertable in the second shell section 14 of the breast receiving funnel 12. An advantage of this arrangement is that it enables the insert 40 to be removed from the funnel 12 and so the funnel 12 and insert 40 can be easily cleaned and/or sterilized. The insert 40 is formed from a resilient material, such as a suitable rubber, silicone elastomer or latex material. Alternatively, the insert 40 is formed from a thermoplastic elastomer.

The insert 40 comprises an upper part 41, a lower part 42 and a circumferentially extending, resiliently deformable wall 43 extending therebetween. The upper part 41 of the insert 40 is located in the mouth 16 of the second shell section 14 when the insert 40 is disposed in the funnel 12 and is removably mounted thereto, as described above for the first exemplary embodiment, such that the upper part 41 is sealed against the second shell section 14. An inner surface 43 of the insert upper part 41 converges on itself to form a conically-shaped hollow section for receiving a user's breast. Similarly, the lower part 42 of the insert 40 is located at the lower end of the throat 17 when the insert 40 is disposed in the funnel 12 and is removably mounted thereto, as described above for the first exemplary embodiment, such that the lower part 42 is sealed against the second shell section 14.

Although in the above embodiment, the insert 40 is removably mountable in the second shell section 14 by the insert upper and lower parts 41,42 respectively overlapping the upper and lower end rims of the second shell section 14 and being held thereon due to the resiliently deformable nature of the insert 40, it will be understood that the invention is not limited thereto and that in alternative embodiments the insert 23 may extend into the second shell section and may be fixedly mounted by an adhesive.

The circumferentially extending, resiliently deformable wall 43 extends between the insert upper and lower parts 41,42 and defines a teat receiving space 45 therein. A user's teat is inserted into the teat receiving space 45 defined by the resiliently deformable wall 43 during use of the insert 40, as will be explained in detail hereinafter.

A flexible corrugated membrane 46 is formed at the upper end of the resiliently deformable wall 43 which extends circumferentially and is integrally formed with the upper part 41 of the insert 40. The upper end of the resiliently deformable wall 43 distends outwardly to the corrugated membrane 46.

The resiliently deformable wall 43 according to the present embodiment comprises a uniform thickness in cross-section. An outer surface 47 of the resiliently deformable wall 43 faces an inner surface 37 of the second shell section 14 and an inner surface 48 of said wall 43 defines the teat receiving space 45.

A first portion 49 of the resiliently deformable wall 43, extending from the upper part 41, is an elliptical frustum shape. Herein, the first portion 49 of the wall 43 is elliptical in cross-section. The first portion 49 converges from the upper part 41 to a second portion 50, which extends between the first portion 49 and the lower part 42, such that the teat receiving space 45 narrows distal to the upper part 41.

The second portion 50 is a cylindrical shape, or alternatively a truncated conical shape, which is circular in cross-section. The first portion 49 and the second portion 50 coalesce and are integrally formed to define the resiliently deformable wall 43.

As the shape of the resiliently deformable wall 26 changes along its length the resistance to deformity increases, such that the deformability of the wall defining the teat receiving space 45 decreases from its upper end to its lower end as the cross-sectional shape of the wall changes from elliptical to circular.

When the insert is disposed in the funnel 12, the outer surface 47 of the resiliently deformable wall 43 and the inner surface 37 of the second shell section 14 in the region of the throat 17 define a pressure chamber therebetween, which will be described in detail below.

Operation of the insert according to the above exemplary embodiment will now be described with reference to FIGS. 9 and 10. Operation of the breast pump and the insert according to this second exemplary embodiment is generally the same as for the first exemplary embodiment, and so a detailed description is omitted herein.

The insert is inserted into the breast pump 1. Although in this second exemplary embodiment a breast pump specially configured to receive an insert as described in detail above is used, it will be understood that in an alternative embodiment the insert is configured for use with a conventional breast pump.

A user inserts the insert 40 into the second shell section 14 of the funnel 12; the insert deforming due to its resilient nature to allow insertion. The insert upper part 41 co-operates with the rim of the second shell section 14 to fixedly mount the upper part 41 to the second shell section 14. Similarly, the insert lower part 42 co-operates with the rim of the lower end of the second shell section 14 to fixedly mount the lower part 42 to the second shell section 14. The outer surface 47 of the resiliently deformable wall 43 and the inner surface 37 (refer to FIG. 3) of the second shell section 14 are spaced from each other to form the pressure chamber which extends circumferentially around the resiliently deformable wall 26 and so circumferentially encompasses the teat receiving space 45. Said pressure chamber extends from the upper part 41 to the lower part 42 of the insert.

The fluid inlet 22 formed in the second shell section 14 provides a fluid communication between the pressure chamber and atmospheric air outside the breast pump. However, in an alternative embodiment the fluid inlet 22 is connected to pressure means (not shown), such as an air pump, to provide a positive pressure differential in the pressure chamber.

Once the insert 40 is inserted in the second shell section 14 of the breast receiving funnel 12, a user then mounts the second shell section 14 to the first shell section 13 to assemble the breast pump 1 and funnel 12. The user inserts a breast into the mouth 16 of the funnel second shell section 14. The user's areola and/or breast locates and seals in the conically-shaped hollow section formed by the upper part 41. Therefore, the user's teat is disposed in the nipple receiving space 45 such that the nipple and areola locate proximate the inner surface 48 of the wall 43.

A negative pressure is formed in the teat receiving space 45 by operating the vacuum pump unit (not shown). The negative pressure helps to induce milk extraction from the user's breast in the manner of a conventional breast pump by applying a negative pressure to the teat, and helps to maintain the breast pump 1 in position relative to the breast even when little or no support is provided externally.

When a negative pressure is applied, the teat is extruded into the teat receiving space 45 such that a substantial portion of the surface of the teat disposed in the teat receiving space 45 is proximate to the inner surface 47 of the resiliently deformable wall 43 of the insert 40.

As the negative pressure is applied in the teat receiving space 45, and the pressure is decreased from an atmospheric pressure, a pressure differential is formed between the teat receiving space 45 and the pressure chamber, which is at atmospheric pressure.

The pressure differential between the teat receiving space 45 and the pressure chamber causes the resiliently deformable wall 43 to distend inwardly into the teat receiving space 45. Due to the difference in shape between the first and second portions 49,50, the second portion 50 has a greater stiffness due to its circular cross-section than the first portion 49, which has a elliptical cross-sectional shape. Therefore, the first portion 49 is caused to distend towards a user's nipple and areola disposed in the teat receiving space 45 prior to the second portion 50 of the wall 20 being deformed and distending into the teat receiving space 45.

As the pressure differential between the teat receiving space 45 and the pressure chamber increases, the elliptical first portion 49 of the resiliently deformable wall 36 is caused to distend inwardly into the teat receiving space 45, and the higher stiffness of the circular second portion 50 prevents said second portion from deforming initially. Subsequently, as the pressure difference increases, a greater portion of the wall 45 is progressively caused to deform and distend inwardly into the teat receiving space 45 as the second portion 50 is caused to deform. Therefore, the wall 40 is caused to progressively distend inwardly from one end of the teat receiving space 45 towards the other end thereof.

As the first portion 49 of the resiliently deformable wall 43 is caused to distend inwardly, the flexible corrugated membrane 46 is caused to expand due to the resilience of the membrane and the corrugation of the membrane being drawn out.

The progressive deformation of the resiliently deformable wall 26 due to the varying cross-sectional shape of the wall 43 as the pressure in the teat receiving space 45 is reduced causes the insert 40 to impart a peristaltic action on a user's teat which promotes the expression of milk from a user's teat and is more analogous to an infant or baby compared with a conventional breast pump action. Furthermore, an advantage of the present invention is that it is only necessary to create a vacuum in the teat receiving space in order for the resiliently deformable wall 43 to distend. Milk is therefore expressed from the user's breast and is expelled from the funnel 12 through the passageway defined by the first and second shell sections 13,14 of the funnel 12 into the main body of the breast pump 1 and into the milk receiving vessel 3.

To cause the resiliently deformable wall 43 to distend outwardly into its original position the pressure in the teat receiving space 45 is increased to reduce the pressure differential between the teat receiving space and the pressure chamber. Therefore, the resiliently deformable wall 43 is urged to distend outwardly into its original position, away from the teat, due to the resilient nature of said wall 43. As the pressure differential is reduced, the second portion 50 of the wall 43 returns to its original shape and position, prior to the first portion 49 returning to its original shape and position due to the difference in stiffness of the first portion 49 compared to the second portion 50.

By cyclically generating a pressure difference in the teat receiving space 45 of the insert 40, a repeated peristaltic action is imparted on a user's teat disposed therein.

An advantage of this arrangement of is that the pressure applied by the insert 40 on the teat disposed in the teat receiving space 45 is non-circular, due to the elliptical cross-section of the first portion 49 of the wall 43 which is analogous to the pressure and action applied by an infant, and so a user is able to change the pressure points on the teat by rotating the breast pump to aid the expression of milk therefrom and to increase comfort.

Although in the above embodiment, the first portion is an elliptical frustum shape and the second portion is a cylindrical shape, it will be understood that the invention is not limited thereto, and that the resiliently deformable wall may be formed in any configuration that enables a first portion of the wall to deform towards a user's teat disposed in the teat receiving space 45 defined by said wall, before a second portion deforms towards said user's teat to provide a peristaltic action on the teat. Furthermore, the wall may be formed from any number of portions that each have a different flexibility as a pressure difference is formed between the pressure chamber and the teat receiving space.

A third exemplary embodiment of the invention will now be described. In this exemplary embodiment, the insert and the breast pump configured to receive the breast pump are generally the same as for the second exemplary embodiment, and so a detailed description is omitted herein. However, in this embodiment the first and second portions of the resiliently deformable wall are formed of different materials with differing stiffness coefficients.

The insert comprises an upper part, a lower part and a circumferentially extending, resiliently deformable wall extending therebetween. The circumferentially extending, resiliently deformable wall extends between the insert upper and lower parts and defines a teat receiving space therein. A user's teat is inserted into the teat receiving space defined by the resiliently deformable wall during use of the insert.

The resiliently deformable wall according to the present embodiment comprises a uniform thickness in cross-section. A first portion of the resiliently deformable wall, extending from the upper part 41, is formed from a first material. The first portion converges from the insert upper part to a second portion, which extends between the first portion and the insert lower part.

The second portion of the resiliently deformable wall is formed from a second material. The second material has a higher stiffness coefficient to the first material and so is less tended to deform. The first portion and the second portion are integrally formed to define the resiliently deformable wall.

As the material from which the resiliently deformable wall changes along its length the stiffness of the resiliently deformable wall changes, such that the stiffness of the wall proximate to its upper end is lower than the stiffness of the wall proximate to its lower end.

Operation of the insert according to the above exemplary embodiment will now be described. Operation of the breast pump and the insert according to this third exemplary embodiment is generally the same as for the first exemplary embodiment, and so a detailed description is omitted herein. Although in this third exemplary embodiment a breast pump specially configured to receive an insert as described in detail above is used, it will be understood that in an alternative embodiment the insert is configured for use with a conventional breast pump.

A user inserts the insert into the second shell section of the funnel and mounts the second shell section to the first shell section; the insert deforming due to its resilient nature to allow insertion. The user inserts a breast into the mouth of the funnel second shell section and the user's areola and/or breast locates and seals in the conically-shaped hollow section formed by the upper part 41.

A negative pressure is formed in the teat receiving space by operating the vacuum pump unit (not shown) and a pressure differential is formed between the teat receiving space and the pressure chamber, which is at atmospheric pressure. Therefore, the teat is extruded into the teat receiving space such that a substantial portion of the surface of the teat disposed in the teat receiving space is proximate to the inner surface of the resiliently deformable wall of the insert.

The pressure differential between the teat receiving space and the pressure chamber causes the resiliently deformable wall to distend inwardly into the teat receiving space. Due to the difference in stiffness of the materials of the first and second portions, the first portion is caused to distend towards a user's teat disposed in the teat receiving space prior to the second portion of the wall being deformed.

As the pressure differential between the teat receiving space and the pressure chamber increases, the first portion of the resiliently deformable wall is caused to distend inwardly into the teat receiving space, and the higher stiffness of the second portion prevents said second portion from initially deforming. Subsequently, as the pressure difference increases, a greater portion of the wall is progressively caused to deform and distend inwardly into the teat receiving space as the second portion is caused to deform. Therefore, the wall is caused to progressively distend inwardly from one end of the teat receiving space towards the other end.

As the first portion of the resiliently deformable wall is caused to distend inwardly, the flexible corrugated membrane is caused to expand due to the resilience of the membrane and the corrugation of the membrane being drawn out.

The progressive deformation of the resiliently deformable wall due to the differing stiffness properties of the first and second materials causes the insert to impart a peristaltic action on a user's teat which promotes the expression of milk from a user's teat and is more analogous to an infant or baby compared with a conventional breast pump action.

To cause the resiliently deformable wall to distend outwardly into its original position the pressure in the teat receiving space is increased to reduce the pressure differential between the teat receiving space and the pressure chamber. As the pressure differential is reduced, the second portion of the wall returns to its original shape and position, prior to the first portion returning to its original shape and position due to the difference in stiffness of the first portion compared to the second portion.

By cyclically generating a pressure difference in the teat receiving space of the insert, a repeated peristaltic action is imparted on a user's teat disposed therein.

Although in the above exemplary embodiments the invention is described as an insert which is insertable in the throat of a breast receiving funnel for a breast pump, it will be understood that the invention is not limited thereto. In alternative embodiments of the invention the insert is formed integral with the throat of a removably mountable funnel, or a funnel integrally formed with a breast pump. In such an embodiment the outer shell is formed from a throat of a funnel and the teat socket is fixedly attached thereto.

Although each of the above embodiments is described independently of each other, it will be apparent to a person skilled in the art that the invention is not limited thereto and that the above embodiments may be combined. In an exemplary embodiment, the resiliently deformable wall comprises first and second portions which are each formed to have a different shape with a different degree of flexibility, and the thickness of the wall varies along its length. Similarly, such inserts may also be formed from a combination of materials with differing stiffness and/or have local thickening.

Although in the above embodiments the inlet is open to atmospheric air such that the pressure in the pressure chamber is an atmospheric pressure, it will be understood that the invention is not limited thereto and that in an alternative embodiment the inlet is connected to pressure generating means (not shown), such as the vacuum pump unit (not shown) disposed in the main body of the breast pump to generate a cyclic pressure in the chamber. Therefore, to create a pressure difference between the pressure chamber and the teat receiving space in this embodiment, it is possible to generate a positive pressure in the pressure chamber which causes the resiliently deformable wall 23,43 to distend towards a teat disposed in the teat receiving space 33, 45 in the peristaltic action discussed above, and so constrict the teat therein. The generation of a positive pressure in the pressure chamber enables the force of the peristaltic movement to be increased.

Although claims have been formulated in this application to particular combinations of features, it should be understood that the scope of the disclosure of the present invention also includes any novel features or any novel combinations of features disclosed herein either explicitly or implicitly or any generalization thereof, whether or not it relates to the same invention as presently claims in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. An insert adapted to fit on a breast-receiving funnel of a breast pump comprising a circumferentially extending resiliently deformable wall which defines a teat receiving space and against which a user's teat is locatable, the insert being configured to define a first pressure chamber and a second pressure chamber, wherein the first pressure chamber is located in the teat receiving space and the second pressure chamber is located between the outer portion of the resiliently deformable wall and a breast receiving funnel when the insert is fitted on a breast receiving funnel, wherein said wall is configured to deform towards a user's teat located in the teat receiving space in a predetermined manner when a pressure difference is applied between the first and second chambers such that a peristaltic action is applied to a user's teat, to aid the expression of milk therefrom, wherein the pressure difference comprises at least a positive pressure applied in the second pressure chamber to generate said peristaltic action.

2. An insert according to claim 1, wherein the wall is configured to deform towards a user's teat located in the teat receiving space in a predetermined manner wherein the pressure difference further comprises a negative pressure applied in the teat receiving space such that a peristaltic action is applied to a user's teat.

3. An insert according to claim 1, wherein the teat receiving space has an opening for receiving a user's teat, and the stiffness of the wall proximate to the opening is lower than the stiffness of the resiliently deformable wall distal to the opening.

4. An insert according to claim 3, wherein the resiliently deformable wall has a diverging wall thickness which increases away from said opening such that a thinner portion of said wall deforms towards said user's teat located in said teat receiving space prior to a thicker portion of said wall deforming towards said user's teat.

5. An insert according to claim 3, wherein a first portion of said wall disposed proximate to the opening is configured to deform towards a user's teat located in said teat receiving space prior to a second portion of said wall distal to said opening deforming towards a user's teat.

6. An insert according to claim 5, wherein the first portion of said wall is an elliptical frustum shape and the second portion is a cylindrical shape such that, when a pressure difference is applied between the teat receiving space and the pressure chamber, the first portion deforms towards said user's breast to apply a positive pressure thereto prior to the second portion deforming towards said user's breast.

7. An insert according to claim 5, wherein the first portion of said wall is formed from a material with a lower stiffness coefficient to the material forming the second portion of said wall.

8. An insert according to claim 5, wherein the resiliently deformable wall extends between mounting means for mounting the insert to a breast receiving funnel which extend circumferentially around upper and lower ends of the wall.

9. An insert according to claim 5, wherein at least one rib extends longitudinally along the resiliently deformable wall to control the collapse of said wall towards the teat.

10. A breast receiving funnel for a breast pump comprising an insert according to claim 5.

11. A breast receiving funnel according to claim 10, comprising a rigid outer shell and a pressure chamber formed between the resiliently deformable wall and the rigid outer shell, the pressure chamber extending around the resiliently deformable wall.

12. A breast receiving funnel according to claim 11, wherein a fluid inlet is formed through the rigid outer shell such that the pressure chamber is open to atmospheric air external to the breast receiving funnel.

13. A breast receiving funnel according to claim 10 wherein the insert is removably mounted to the funnel.

14. A breast pump comprising a breast receiving funnel according to claim 13, the breast pump including means for generating a negative pressure in the funnel when a user's breast is received therein.

15. A breast pump according to claim 10, further comprising means to apply a positive pressure in said pressure chamber to urge the resiliently deformable wall to deform towards a user's teat when the pressure in said pressure chamber is increased.

* * * * *